United States Patent
Fukumoto et al.

(10) Patent No.: US 6,673,733 B2
(45) Date of Patent: *Jan. 6, 2004

(54) METHOD FOR REGENERATING HETEROPOLYACID CATALYST AND METHOD FOR PRODUCING METHACRYLIC ACID

(75) Inventors: Naohiro Fukumoto, Hyogo-ken (JP); Naomasa Kimura, Okayama-ken (JP); Hiroto Kasuga, Hyogo-ken (JP); Eiichi Shiraishi, Hyogo-ken (JP)

(73) Assignee: Nippon Shokubai Co., Ltd., Osaka (JP)

( * ) Notice: Subject to any disclaimer, the term of this patent is extended or adjusted under 35 U.S.C. 154(b) by 254 days.

This patent is subject to a terminal disclaimer.

(21) Appl. No.: 09/824,338

(22) Filed: Apr. 3, 2001

(65) Prior Publication Data

US 2001/0039240 A1 Nov. 8, 2001

(30) Foreign Application Priority Data

Apr. 6, 2000 (JP) .......................... 2000-104487

(51) Int. Cl.[7] .......................... B01J 38/66; B01J 20/34; B01J 38/50; B01J 27/19; C07C 51/16
(52) U.S. Cl. .......................... 502/26; 502/27; 502/29; 502/211; 562/535
(58) Field of Search .......................... 502/26, 27, 29, 502/211; 562/535

(56) References Cited

U.S. PATENT DOCUMENTS

| | | | |
|---|---|---|---|
| 4,621,155 A | * 11/1986 | Ueshima et al. ............ | 562/534 |
| 4,814,305 A | 3/1989 | Kamogawa et al. .......... | 502/26 |
| 5,138,108 A | 8/1992 | Tustin et al. ................ | 570/203 |
| 5,716,895 A | * 2/1998 | Sugi et al. ................... | 502/24 |
| 6,458,740 B2 | * 10/2002 | Kasuga et al. .............. | 502/211 |

FOREIGN PATENT DOCUMENTS

| | | |
|---|---|---|
| DE | 3708625 A1 | 10/1988 |
| EP | 0 268 201 A1 | 5/1988 |
| JP | 450062 | 8/1992 |

OTHER PUBLICATIONS

Derwent Publications Ltd., London, GB;1978–42922A (Abstr. of JP 53,049234 A.

* cited by examiner

Primary Examiner—Stanley S. Silverman
Assistant Examiner—Jonas N. Strickland
(74) Attorney, Agent, or Firm—Sherman & Shalloway

(57) ABSTRACT

The invention provides a method for regenerating with high efficiency a deteriorated catalyst of reduced activity, said catalyst originating from a heteropolyacid catalyst containing heteropolyacid formed of molybdophosphoric acid and/or molybdovanadophosphoric acid, or a salt thereof, to a heteropolyacid catalyst which exhibits approximately equivalent activity level to that of the fresh catalyst. Said method comprises mixing a deteriorated catalyst and a nitrogen-containing heterocyclic compound under the conditions whereunder ammonium ions and nitrate anions are present at such ratio that the amount of total ammonium ions per mol of total nitrate anions does not exceed 1.7 mols, drying the mixture and calcining the same.

8 Claims, No Drawings

METHOD FOR REGENERATING HETEROPOLYACID CATALYST AND METHOD FOR PRODUCING METHACRYLIC ACID

TECHNICAL FIELD TO WHICH THE INVENTION BELONGS

This invention relates to a method for regenerating heteropolyacid catalyst and method for producing methacrylic acid. More particularly, the invention relates to a method for regenerating heteropolyacid catalyst whose activity has been deteriorated due to, for example, prolonged use for catalytic vapor phase oxidation reaction; and also to a method for producing methacrylic acid through vapor phase oxidation or vapor phase oxidative dehydrogenation of methacrolein, isobutyl aldehyde and/or isobutyric acid in the presence of the regenerated heteropolyacid catalyst.

PRIOR ART

Heretofore, heteropolyacid catalyst whose chief component is a heteropolyacid composed of molybdophosphoric acid (phosphorus-molybdenum) or molybdovanadophosphoric acid (phosphorus-molybdenum-vanadium), or a salt thereof has been used for producing methacrylic acid through vapor phase oxidation of methacrolein, isobutyl aldehyde or isobutyric acid and the like.

It is normal for industrial scale vapor phase oxidation reaction to be conducted continuously over a prolonged period, and during which the catalyst used in the reaction is subject to severe thermal load. This induces undesirable physical and chemical changes in the catalyst and consequently deterioration of the catalyst progresses to gradually render continuation of the reaction difficult. Hence the deteriorated catalyst must be taken out of the reaction tube after a prescribed period of time and a newly prepared catalyst, be re-filled. The cost of the catalyst in that occasion incurs a heavy economical burden. This situation is same for production of methacrylic acid through vapor phase oxidation of methacrolein, isobutylaldehyde or isobutyric acid and the like, using a heteropolyacid catalyst.

It is therefore generally important from economical standpoint to regenerate the catalyst whose activity is reduced, and various proposals have been made for regeneration of deteriorated heteropolyacid catalyst. For example, Official Gazette of Patent Publication Hei 4(1992)-50062B1-JP describes a method for regenerating deteriorated catalyst by a treatment with a nitrogen-containing heterocyclic compound such as pyridine. Also Official Gazette of Patent Publication Hei 7(1995)-20552B1-JP (=U.S. Pat. No. 4,814,305) teaches a method of regenerating the deteriorated catalyst which contains phosphorus, molybdenum and alkali metal, by a treatment with an aqueous solution containing aqueous ammonia, amine and the like, followed by drying and calcination.

However, the cause of deterioration of heteropolyacid catalyst has not yet been made clear. Above-referenced Official Gazettes also contain no concrete disclosure about the cause of the deterioration. The invention of Hei 4-50062B1-JP, therefore, judges the end of its regeneration treatment by conducting the following three measurements of the regenerated catalyst: (1) X-ray diffraction measurement—as for deteriorated catalyst, diffraction lines attributable to molybdenum trioxide are found, which are not found with the same catalyst before deterioration (fresh catalyst). The regeneration is judged to be complete, when such diffraction lines disappear as the result of the regeneration treatment and the X-ray diffraction chart which is the same to that of the fresh catalyst is obtained; (2) BET specific surface area measurement—a deteriorated catalyst has a specific surface area reduced to about 60% of that of the fresh catalyst. When it recovers to approximately the same level to that of the fresh catalyst as the result of the regeneration treatment, the treatment is judged to have been completed; and (3) activity level measurement—when a deteriorated catalyst comes to show equivalent performance in the reaction to that of the fresh catalyst in consequence of the regeneration treatment, the treatment is deemed to be complete. The invention of Hei 7-20552B1-JP (=U.S. Pat. No. 4,814,305) also confirms completion of the regeneration based on similar measurements as above.

PROBLEMS TO BE SOLVED BY THE INVENTION

As above, reduction in the costs for catalyst notably contributes to cut down the production costs, and development of a new regeneration method which can substantially improve those heretofore known methods is in demand. Thus, as to heteropolyacid catalyst also a method for regenerating deteriorated catalyst with high efficiency is desired, which enables the deteriorated catalyst to exhibit approximately equivalent activity to that of the fresh catalyst and furthermore to maintain that activity for a long period.

Accordingly, therefore, one of the objects of the present invention is to provide a method for regenerating a deteriorated heteropolyacid catalyst to one having the same composition with that of the fresh catalyst.

Another object of the invention is to provide a method for regenerating a deteriorated heteropolyacid catalyst to one having a different composition from that of the starting fresh catalyst, i.e., a method for preparing a new heteropolyacid catalyst, using the deteriorated heteropolyacid catalyst as the starting material.

Still other object of the invention is to provide a method for preparing methacrylic acid through catalytic vapor phase oxidation of methacrolein, isobutylaldehyde and/or isobutyric acid, using the catalyst which is regenerated by either of the above methods.

MEANS TO SOLVE THE PROBLEMS

We have found that the causes for deterioration of heteropolyacid catalysts after prolonged use are: (1) of the components constituting them, particularly those heteropolyacid-constituting components such as phosphorus, molybdenum and vanadium scatter and are lost, and in consequence composition notably changes from that of the fresh catalyst; (2) specific surface area is reduced; and (3) a part of the heteropolyacid structure is collapsed. We have accordingly pursued studies on replenishment of the scattered and lost heteropolyacid-constituting elements into the deteriorated catalyst, to discover that the disappeared heteropolyacid-constituting elements can be effectively replenished by treating the deteriorated catalyst in the presence of a nitrogen-containing heterocyclic compound under the conditions wherein ammonium ions and nitrate ions are present at a specific ratio; that the so obtained regenerated heteropolyacid catalyst has approximately the same specific surface area to that of the fresh catalyst; that X-ray diffraction chart of the regenerated heteropolyacid catalyst is approximately the same to that of the fresh catalyst, indicating recovery of the collapsed heteropolyacid structure; and that a catalyst, which is deteriorated because of partial collapse of its heteropolyacid structure under excessive thermal load although retaining its composition unaffected, can also exhibit the catalytic performance and have the structure regenerated by a similar treatment. The present invention is completed based on these discoveries.

Thus, according to the invention, as a method for regenerating a deteriorated catalyst whose activity attributable to a heteropolyacid catalyst containing heteropolyacid composed of molybdophosphoric acid and/or molybdovanadophosphoric acid or salt(s) thereof is reduced, a method is provided which is characterized by mixing the deteriorated catalyst with a nitrogen-containing heterocyclic compound under such conditions that ammonium ions and nitrate anions are present at such a ratio that the total amount of the ammonium ions present per mol of the total amount of the nitrate anions does not exceed 1.7 mols, drying the mixture and calcining the same.

According to the invention, furthermore, a method for preparation of methacrylic acid through catalytic vapor phase oxidation of methacrolein, isobutyl aldehyde and/or isobutyric acid is provided, said method being characterized by use of a catalyst which is regenerated by the above-described method.

The regeneration method of the invention is useful for regenerating heteropolyacid catalysts whose activity has been deteriorated for various reasons. In particular, the method is conveniently used for regenerating heteropolyacid catalysts whose activity has been deteriorated by use over a prolonged period.

EMBODIMENTS OF THE INVENTION

The regeneration method of the invention is applicable to any deteriorated catalysts so long as they originate from heteropolyacid catalysts useful for vapor phase oxidation reaction of organic compounds. Whereas, the method is preferably applied for regenerating deteriorated catalysts originating from heteropolyacid catalysts which were used in vapor phase oxidation of unsaturated aldehydes (in particular, methacrolein, isobutyl aldehyde and/or isobutyric acid) for producing corresponding unsaturated carboxylic acids (in particular, methacrylic acid).

The heteropolyacid catalysts which are referred to in the invention contain a heteropolyacid whose essential constituent elements are phosphorus-molybdenum, or phosphorus-molybdenum-vanadium, or a salt of such an acid. In particular, those heteropolyacid catalysts to which the regeneration method of the invention is most conveniently applicable are expressed by the following formula (I):

$$P_aMo_bV_cX_dY_eO_f \qquad (I)$$

(wherein Mo, V, P and O are molybdenum, vanadium, phosphorus and oxygen, respectively; X stands for at least one element selected from the group consisting of potassium, rubidium, cesium and thallium; Y is at least an element selected from the group consisting of alkaline earth metals, copper, silver, arsenic, antimony, bismuth, iron, cobalt, nickel, chromium, manganese, tungsten, zirconium, niobium, titanium, zinc, tin, selenium, tellurium, germanium, palladium, rhodium, rare earth elements and silicon; and suffixes a, b, c, d, e and f denote atomic ratios of the respective elements, where when b is 12, a, c, d and e each is a value not more than 3 but not including 0 (zero), and f is a value determined by valencies and atomic ratios of those elements other than oxygen).

Such heteropolyacid catalyst can be prepared by processes well known in the art.

The characteristic feature of the invention resides in mixing such a deteriorated catalyst with a nitrogen-containing heterocyclic compound under the conditions that ammonium ions and nitrate anions are present at such ratios that the total amount of the ammonium ions does not exceed 1.7 mols per mol of the total amount of the nitrate anions (i.e., at a molar ratio of total amount of ammonium ions/total amount of the nitrate anions $\leq 1.7$), preferably at a ratio between 0.01 and 1.7 mols, inter alia, between 0.1 and 1.6 mols. By the treatment comprising the characteristic step, partially collapsed heteropolyacid structure due to, for example, excessive thermal load is regenerated, and consequently the deteriorated catalyst regains its catalytic performance (cf. Example 9 which appears later). Where the total amount of the ammonium ions per mol of the total amount of the nitrate anions exceeds 1.7 mols, satisfactory regeneration effect cannot be accomplished.

According to the regeneration method of the present invention, it is also preferred that the total amount of the ammonium ions per 12 mols of the molybdenum atoms should not exceed 15 mols, more conveniently lies within the range of 0.1–15 mols, inter alia, in the range of 2–14 mols. Therefore, in a preferred embodiment of the present invention, a deteriorated catalyst and a nitrogen-containing heterocyclic compound are mixed under such conditions that ammonium ions and nitrate anions are present in the mixture at such a ratio that the total amount of the ammonium ions per mol of the total amount of the nitrate anions does not exceed 1.7 mols (preferably 0.01–1.7 mols, inter alia, 0.1–1.6 mols) and said total amount of the ammonium ions per 12 mols of the molybdenum atoms does not exceed 15 mols (in particular, 0.1–15 mols, inter alia, 2–14 mols).

According to the regeneration method of the invention, furthermore, it is preferred to concurrently mix, in the occasion of mixing a deteriorated catalyst with a nitrogen-containing heterocyclic compound, compounds containing the constituent elements of the original catalyst and/or a compound or compounds containing the element(s) other than those constituent elements of the original catalyst. Use of those compounds containing the constituent elements of the original heteropolyacid catalyst enables to regenerate the deteriorated catalyst, whose constituent elements have scattered and lost, to a heteropolyacid catalyst having the identical composition with that of the original heteropolyacid catalyst. Whereas, use of those compounds containing the constituent elements of the original catalyst and a compound or compounds containing element(s) other than those constituting the original catalyst; or use of the latter compound alone enables to regenerate the deteriorated heteropolyacid catalyst to a catalyst having a different composition from that of the original heteropolyacid catalyst. In the latter embodiment of the regeneration method, a heteropolyacid catalyst having a composition different from that of the deteriorated heteropolyacid catalyst is prepared anew.

Methods for causing presence of nitrate anions and ammonium ions in the mixture at such ratios that the total amount of the ammonium ions per mol of the total amount of the nitrate anions does not exceed 1.7 mols are subject to no critical limitation, but it can be achieved by various methods. For example, as a source for ammonium ion supply, ammonium nitrate, ammonium carbonate, ammonium bicarbonate, ammonium acetate and the like may be used, or for supplementing a certain element, an ammonium salt of said element may be newly added.

Hereinafter the regeneration method of the invention is explained, referring to examples of mixing a deteriorated catalyst and a nitrogen-containing heterocyclic compound, concurrently with compounds containing the constituent elements of the original heteropolyacid catalyst and/or a compound or compounds containing element(s) other than those constituting the original heteropolyacid catalyst.

One of the embodiments of the regeneration method of the invention ("regeneration process A" which is described in the following) uses compounds containing the same constituent elements to those of the original heteropolyacid catalyst, according to which the deteriorated heteropolyacid catalyst is regenerated to the one having the same composition to that of the original heteropolyacid catalyst. Whereas, the other embodiment of the regeneration method of the invention ("regeneration process B" which is described later) uses compounds containing the same constituent elements to those of the original heteropolyacid catalyst and a compound or compounds containing element(s) other than those constituting the original heteropolyacid catalyst, or uses the latter compound alone, according to which the deteriorated catalyst is regenerated to a heteropolyacid catalyst having a composition different from that of the original heteropolyacid catalyst as aforesaid.

Regeneration Process A

Both a fresh catalyst and the same catalyst after deterioration are subjected to compositional analysis by means of X-ray fluorescence diffractiometry, to calculate the amounts of the constituent elements (e.g., phosphorus and molybdenum, or phosphorus, molybdenum and vanadium) which have been scattered away and lost to cause the deterioration. Then the deteriorated catalyst is treated with the compounds containing the lost constituent elements of the amounts necessary to replenish the loss, i.e., of the amounts necessary for obtaining an identical composition (identical constituent elements and their constituting ratio) with that of the fresh catalyst, and also a nitrogen-containing heterocyclic compound in the presence of ammonium ions and nitrate anions.

As typical examples of nitrogen-containing heterocyclic compound, pyridine, piperidine, piperazine, pyrimidine, isoquinoline and derivatives of the those compounds (alkyl-substituted derivatives) may be named. These compounds are preferably used in the form of inorganic salts thereof, such as nitrate, sulfate, chloride and the like (cf. Hei 4(1992)-50062B1-JP). The use rate of such a nitrogen-containing heterocyclic compound can be suitably selected within a range of 1–50% by weight of the deteriorated catalyst.

As the compounds containing the lost constituent elements, those raw materials which are conventionally used for preparation of heteropolyacid containing phosphorus and molybdenum, or containing phosphorus, molybdenum and vanadium, such as those in the form of salts or oxides, can be used. For example, as phosphorus-containing raw materials, phosphoric acid, ammonium phosphate and the like may be used; as molybdenum-containing raw materials, ammonium molybdate, molybdenum trioxide, molybdic acid and the like; and as vanadium-containing compounds, ammonium metavanadate and the like. The use rates of those compounds containing the lost constituent elements are suitably determined depending on the lost amounts of the constituent elements so as to replenish the lost elements and provide a regenerated catalyst having identical composition with that of the fresh catalyst.

The treatment of a deteriorated catalyst with above-described nitrogen-containing heterocyclic compound and compounds containing the lost constituent elements comprises preparing a mixture of the deteriorated catalyst, nitrogen-containing heterocyclic compound and compounds containing the lost constituent elements in the presence of ammonium ions and nitrate anions, drying the mixture and calcining the same. More specifically, the treatment comprises, for example, dispersing a deteriorated catalyst in water, adding a nitrogen-containing heterocyclic compound and compounds containing the lost constituent elements thereto, adjusting the amounts of ammonium ions and nitrate anions, thereafter concentrating the mixture under stirring, drying the concentrate at temperatures ranging 100–300° C., normally optionally shaping the dried product and calcining the same at temperatures ranging 200–600° C. In that occasion, the drying may be followed by calcination in an inert gas such as nitrogen at 200–600° C., and further in air at 100–400° C., following the process described in Hei 4-50062B1-JP.

According to the above regeneration process A, a deteriorated catalyst can be regenerated to a catalyst having identical composition with that of the fresh catalyst. This regenerated catalyst has approximately the same specific surface area to that of the fresh catalyst as shown in later given working examples, and exhibits approximately same physical properties as verified by the absence of the diffraction lines attributable to molybdenum trioxide in its X-ray diffraction chart.

Moreover, according to the regeneration process A, besides regenerating a deteriorated catalyst to one having identical composition with that of the fresh catalyst as above, it is also possible to regenerate to a catalyst formed of same constituent elements to those of the fresh catalyst but at different ratios (atomic ratios). The regeneration process A also encompasses such embodiments.

Regeneration Process B

In regeneration process B, a deteriorated catalyst is treated with a nitrogen-containing heterocyclic compound, compounds containing the constituent elements of the original catalyst and a compound(s) containing element(s) other than the constituent elements of the original catalyst; or with a nitrogen-containing heterocyclic compound and a compound(s) containing element(s) other than the constituent elements of the original catalyst. According to this process, the deteriorated catalyst is regenerated to a catalyst of a composition (constituent elements) differing from that of the original catalyst.

As examples of compounds containing elements other than the constituent elements of the original catalyst, those containing the metal elements constituting heteropolyacid salts in general, e.g., those containing such metal elements as alkali metals, alkaline earth metals, copper, silver, arsenic, antimony, bismuth, iron, cobalt, nickel, chromium, manganese, tungsten, zirconium, niobium, titanium, zinc, tin, selenium, tellurium, germanium, palladium, rhodium, rare earth elements, silicon, and the like. These compounds can be used in the form of nitrates, carbonates, sulfates, chlorides, hydroxides, oxides and the like.

The regeneration process B can be practiced in the manner similar to the regeneration process A, except the point that the above compound(s) containing element(s) other than the constituents of the original catalyst is used. That is, a mixture of a deteriorated catalyst, a nitrogen-containing heterocyclic compound, compounds containing the constituent elements of the original catalyst and a compound(s) containing element(s) other than the constituent elements of the original catalyst; or a mixture of a deteriorated catalyst, a nitrogen-containing heterocyclic compound and a compound(s) containing element(s) other than the constituent elements of the original catalyst; is prepared in the presence of ammonium ions and nitrate anions, said mixture then being dried and calcined. The use rates of the compounds containing the constituent elements of the original catalyst and/or the compound(s) containing the element(s) other than the constituent elements of the original catalyst can be suitably determined depending on the intended composition of the regenerated catalyst.

Regenerated catalysts obtainable through the regeneration method of the invention exhibit similar catalytic performance to that of the original catalysts, and are conveniently used, either by itself or as mixed with fresh catalyst, in vapor phase oxidation reaction of organic compounds, in particular, in methacrylic acid-forming reaction by vapor phase oxidation of methacrolein, isobutyl aldehyde and/or isobutyric acid.

EFFECT OF THE INVENTION

According to the regeneration method of the invention, regenerated catalysts which exhibit markedly higher catalytic activity and, if necessary, physical properties approximately equivalent to those of fresh catalysts are obtained, as compared to those regenerated catalysts obtained by conventional regeneration method comprising treating a deteriorated catalyst with a nitrogen-containing heterocyclic compound alone or the one comprising replenishing a deteriorated catalyst with its decreased constituent elements in the absence of a nitrogen-containing heterocyclic compound.

EXAMPLES

Hereinafter the present invention is explained more specifically, referring to working Examples, wherein the conversion, selectivity and one-pass yield have the following definitions.

Conversion (mol %)=(mol number of reacted methacrolein)/(mol number of supplied methacrolein)×100

Selectivity (mol %)=(mol number of formed methacrylic acid)/(mol number of reacted methacrolein)×100

One-pass yield (mol %)=(mol number of formed methacrylic acid)/(mol number of supplied methacrolein)×100

Example 1

(Catalyst Preparation)

To 2,800 ml of 60° C. water, 1,236 g of ammonium paramolybdate and 68.2 g of ammonium matavanadate were dissolved and stirred, followed by further addition of 280 g of pyridine and 87.4 g of phosphoric acid (85%), and a solution of 770 g of nitric acid (65%), 136.4 g of cesium nitrate and 14.1 g of copper nitrate as dissolved in 1,000 ml of water, by the order stated. This aqueous mixture was concentrated under heating and stirring, and the resulting clay-like substance was molded into columns of each 5 mm in diameter and 6 mm in height, which were dried at 120° C. for 15 hours and calcined in a gaseous nitrogen stream at 430° C. for 4 hours, and then in an air stream at 400° C. for 2 hours. The composition of so obtained catalyst was given an X-ray fluorescence analysis to be found as, in terms of atomic ratios of the metal elements excluding oxygen, P:Mo:V:Cu:Cs=1.3:12:1:0.1:1.2. Upon X-ray diffraction (per cathode Cu—Kα) measurement, the catalyst was found to be composed mainly of molybdovanadophosphoric acid and its partial metal salt. The BET specific surface area of the catalyst and presence or absence of X-ray diffraction lines attributable to molybdenum trioxide ($MoO_3$) in its diffraction chart are indicated in Table 1.

(Deterioration)

A following deterioration-accelerating test was given to 750 ml of above-obtained catalyst continuously for 5,000 hours. Upon analyzing the composition of the resultant deteriorated catalyst using X-ray fluorescence, the atomic ratios of the metal elements excluding oxygen were found to be: P:Mo:V:Cu:Cs=1.10:9.8:0.98:0.1:1.2, markedly differing from the composition of the fresh catalyst. According to X-ray diffractiometry thereof, strong diffraction lines attributable to molybdenum trioxide appeared in the vicinities of 2θ=27.3, 12.7, 23.3 and 25.60, which were entirely absent in the diffraction chart of the fresh catalyst, indicating that the heteropolyacid structure was partially collapsed. The BET specific surface area of the deteriorated catalyst and the presence of X-ray diffraction lines attributable to molybdenum trioxide are indicated in Table 1.

<Deterioration-Accelerating Test>

750 Milliliters of above catalyst was filled in a stainless steel reaction tube of 25 mm in inner diameter. The tube was immersed in a molten salt bath of 380° C., and through which a starting gaseous mixture of the composition:methacrolein:oxygen:nitrogen:water= 2:6:32:10 by volume ratio, was passed at a space velocity of 2,000 $h^{-1}$ (STP) continuously for 5,000 hours.

(Regeneration Treatment)

One-hundred (100) g of the deteriorated catalyst was dispersed in 200 ml of water and stirred at 70° C. As the differences in components' quantities between the fresh catalyst and the deteriorated catalyst as determined by the X-ray fluorescence analysis, 22.2 g of ammonium paramolybdate, 1.3 g of phosphoric acid (85%) and 0.13 g of ammonium metavanadate were added to the dispersion, followed by addition of 40 g of ammonium nitrate, 15 g of pyridine and 15 g of nitric acid (65%). The aqueous mixture was concentrated under stirring. The total amount of ammonium ions at the time of preparing the mixture was 10.67 mols per 12 mols of molybdenum atoms, and the total ammonium ions/total nitrate anions (molar ratio) was 0.93. Thus obtained clay-like substance was dried at 200° C., molded into columns of each 5 mm in diameter and 6 mm in height, and which were dried at 200° C. and calcined in gaseous nitrogen stream at 430° C. for 3 hours, and then in an air stream at 400° C. for 2 hours. Whereupon a regenerated catalyst was obtained. An X-ray fluorescence analysis of the catalyst composition found that the atomic ratios of the metal elements excepting oxygen were: P:Mo:V:Cu:Cs= 1.3:12:1:0.1:1.2. In the diffraction chart of this regenerated catalyst, the diffraction lines attributable to molybdenum trioxide which were seen in the chart of the deteriorated catalyst completely disappeared, and other diffraction lines identical with those of the fresh catalyst were indicated. The BET specific surface area and the presence or absence of the diffraction lines attributable to molybdenum trioxide are shown in Table 1.

<Performance Test>

Fifty (50) ml of the regenerated catalyst was charged in a U-shaped stainless steel tube of 25 mm in inner diameter, and the tube was immersed in a 280° C. molten salt bath. Through said tube a starting gaseous mixture of methacrolein: oxygen: nitrogen: water=1:3:36:10 by volume ratio was passed at a space velocity of 1,000 $h^{-1}$ (STP). The result was as shown in Table 1.

From Table 1, it can be understood that the regenerated catalyst has approximately the same physical properties to those of the fresh catalyst, and that the former's catalytic performance also is approximately equivalent to that of the fresh catalyst.

Example 2

In the occasion of regeneration treatment in Example 1, the amount of the ammonium nitrate was decreased from 40 g to 15 g, and otherwise the treatment of Example 1 was repeated. The amount of total ammonium ions at the time of preparing the mixture was, per 12 mols of molybdenum atoms, 5.19 mols, and the total ammonium ions/total nitrate anions (molar ratio) was 0.87. The result was as shown in Table 1.

Example 3

In the occasion of regeneration treatment in Example 1, the amount of the ammonium nitrate was decreased from 40 g to 5 g, and otherwise the treatment of Example 1 was repeated. The amount of total ammonium ions at the time of the mixture preparation was, per 12 mols of molybdenum atoms, 3.00 mols, and the total ammonium ions/total nitrate anions (molar ratio) was 0.79. The result was as shown in Table 1.

Example 4

In the occasion of regeneration treatment in Example 1, no nitric acid was added (nitric acid=0 g), and the amount of the ammonium nitrate was decreased from 40 g to 20 g. Otherwise the treatment of Example 1 was repeated. The amount of total ammonium ions at the time of mixture preparation was, per 12 mols of molybdenum atoms, 6.29 mols, and the total ammonium ions/total nitrate anions (molar ratio) was 1.43. The result was as shown in Table 1.

Example 5

The regeneration treatment in Example 3 was repeated except that the amount of nitric acid was increased from 15 g to 55 g. The amount of total ammonium ions at the time of the mixture preparation was, per 12 mols of molybdenum atoms, 3.00 mols, and the total ammonium ions/total nitrate anions (molar ratio) was 0.27. The result was as shown in Table 1.

Example 6

The regeneration treatment in Example 1 was repeated except that 22.1 g of ammonium paramolybdate was replaced with 18.1 g of molybdenum trioxide. The amount of total ammonium ions at the time of mixture preparation was, per 12 mols of molybdenum atoms, 8.78 mols, and the total ammonium ions/total nitrate anions (molar ratio) was 0.77. The result was as shown in Table 1.

Examples 7–8

The regeneration treatment in Example 1 was repeated, except that the pyridine was changed to equal amount of piperidine or piperazine, respectively. The results were as shown in Table 1.

Example 9

(Thermal Degradation)

The fresh catalyst as obtained in Example 1 was further calcined in air at 650° C. for 2 hours. The composition of thus obtained thermally degraded catalyst as determined by X-ray fluorescence analysis was, in terms of the atomic ratios of the metal elements excepting oxygen, P:Mo:V:Cu:Cs=1.3:12:1:0.1:1.2, which was same to that of the fresh catalyst. However, according to the result of X-ray diffractiometry, diffraction lines attributable to molybdenum trioxide appeared, indicating that a part of the heteropoly-acid structure was collapsed. The BET specific surface area of the thermally degraded catalyst and presence or absence of the X-ray diffraction lines attributable to molybdenum trioxide were indicated in Table 1.

(Regeneration Treatment)

The regeneration treatment of Example 1 was repeated except that 100 g of the above thermally degraded catalyst was used instead of 100 g of the deteriorated catalyst and none of ammonium paramolybdate, phosphoric acid and ammonium metavanadate was added. The total amount of ammonium anions at the time of the mixture preparation was, per 12 mols of molybdnum atoms, 10.56, and the total ammonium ions/total nitrate anions (molar ratio) was 0.76. The result was as shown in Table 1.

Comparative Example 1

The regeneration treatment of Example 9 was repeated except that the 40 g of ammonium nitrate was replaced by 40 g of ammonium acetate. The amount of total ammonium ions at the time of the mixture preparation was, per 12 mols of molybdnum atoms, 10.96, and the total ammonium ions/total nitrate anions (molar ratio) was 3.36.

Comparative Example 2

The regeneration treatment of Example 9 was repeated except that the addition of pyridine was omitted. The amount of total ammonium ions at the time of the mixture preparation was, per 12 mols of molybdnum atoms, 10.56 mols, and the total ammonium ions/total nitrate anions (molar ratio) was 0.76.

TABLE 1

| | $NH_4/Mo_{12}$ molar ratio | $NH_4/NO_3$ molar ratio | Methacrolein conversion (mol %) | Methacrylic acid selectivity (mol %) | Methacrylic acid one-pass yield (mol %) | BET specific surface area ($m^2/g$) | $MoO_3$ on XRD |
|---|---|---|---|---|---|---|---|
| Example 1 | | | | | | | |
| fresh catalyst | — | — | 88.7 | 88.3 | 78.3 | 5.0 | no |
| deteriorated catalyst | — | — | 35.6 | 48.5 | 17.3 | 1.7 | yes |
| regenerated catalyst | 10.67 | 0.93 | 89.2 | 88.0 | 78.5 | 5.2 | no |
| Example 2 | 5.19 | 0.87 | 89.0 | 88.0 | 78.3 | 5.1 | no |
| Example 3 | 3.00 | 0.79 | 88.1 | 88.7 | 78.1 | 5.0 | no |
| Example 4 | 6.29 | 1.43 | 88.5 | 88.9 | 78.7 | 4.9 | no |
| Example 5 | 3.00 | 0.27 | 89.0 | 88.3 | 78.6 | 5.1 | no |
| Example 6 | 8.78 | 0.77 | 88.6 | 88.5 | 78.4 | 5.3 | no |

TABLE 1-continued

|  | $NH_4/Mo_{12}$ molar ratio | $NH_4/NO_3$ molar ratio | Methacrolein conversion (mol %) | Methacrylic acid selectivity (mol %) | Methacrylic acid one-pass yield (mol %) | BET specific surface area (m²/g) | $MoO_3$ on XRD |
|---|---|---|---|---|---|---|---|
| Example 7 | 10.67 | 0.93 | 88.2 | 88.5 | 78.1 | 5.2 | no |
| Example 8 | 10.67 | 0.93 | 88.9 | 88.0 | 78.2 | 5.0 | no |
| Example 9 |  |  |  |  |  |  |  |
| thermally degraded catalyst | — | — | 19.8 | 42.1 | 8.3 | 1.9 | yes |
| regenerated catalyst | 10.56 | 0.76 | 88.9 | 88.1 | 78.3 | 5.0 | no |
| Comparative Example 1 | 10.96 | 3.36 | 92.3 | 53.4 | 49.3 | 4.3 | no |
| Comparative Example 2 | 10.56 | 0.76 | 23.5 | 39.5 | 9.3 | 2.8 | no |

Example 10

The regeneration treatment of Example 1 was repeated except that the silver nitrate was added simultaneously with the ammonium metavanadate, to make the P:Mo:V:Cu:Cs:Ag ratios 1.3:12:1:0.1:1.2:0.1. The result was as shown in Table 2.

Example 11

The regeneration treatment of Example 1 was repeated except that zirconyl oxynitrate was added simultaneously with the ammonium metavanadate, to make the P:Mo:V:Cu:Cs:Zr ratios 1.3:12:1:0.1:1.2:0.1. The result was as shown in Table 2.

Example 12

The regeneration treatment of Example 1 was repeated except that zinc oxide was added simultaneously with the ammonium metavanadate, to make the P:Mo:V:Cu:Cs:Zn ratios 1.3:12:1:0.1:1.2:0.1. The result was as shown in Table 2.

Referential Examples 1–3

Catalysts were prepared in the identical manner with Example 1, except that the silver nitrate, zirconyl oxynitrate and zinc oxide, respectively, was added after addition to the aqueous solution of cesium nitrate and copper nitrate. Thus formed catalysts had identical compositions with those of the catalysts obtained in Examples 10, 11 and 12, respectively. The results were as shown in Table 2.

TABLE 2

|  | $NH_4/Mo_{12}$ molar ratio | $NH_4/NO_3$ molar ratio | Methacrolein conversion (mol %) | Methacrylic acid selectivity (mol %) | Methacrylic acid one-pass yield (mol %) | BET specific surface area (m²/g) | $MoO_3$ on XRD |
|---|---|---|---|---|---|---|---|
| Example 10 | 10.67 | 0.92 | 89.6 | 86.6 | 77.6 | 4.8 | no |
| Referential Example 1 | — | — | 89.5 | 86.4 | 77.3 | 4.9 | no |
| Example 11 | 10.67 | 0.91 | 91.6 | 83.2 | 76.2 | 5.1 | no |
| Referential Example 2 | — | — | 92.0 | 83.1 | 76.5 | 5.1 | no |
| Example 12 | 10.67 | 0.93 | 85.1 | 88.5 | 75.3 | 5.0 | no |
| Referential Example 3 | — | — | 84.8 | 88.7 | 75.2 | 4.9 | no |

What is claimed is:

1. A method for regenerating a deteriorated catalyst of reduced activity, said catalyst originating from a heteropolyacid catalyst containing heteropolyacid formed of a molybdophosphoric acid and/or molybdovanadophosphoric acid, or a salt thereof, said method comprising mixing the deteriorated catalyst with a nitrogen-containing heterocyclic compound under such conditions that ammonium ions and nitrate anions are present at such ratios that the amount of total ammonium ions per mol of total nitrate anions does not exceed 1.7 mols, drying the resulting mixture and calcining the same.

2. A method according to claim 1, in which the deteriorated catalyst and a nitrogen-containing heterocyclic compound are mixed under such conditions that ammonium ions and nitrate anions are present at such ratios that the amount of total ammonium ions per mol of total nitrate anions does not exceed 1.7 mols and as the amount of total ammonium ions per 12 mols of molybdenum atoms does not exceed 15 mols.

3. The method according to claim 2, wherein the deteriorated catalyst and the nitrogen-containing heterocyclic compound are mixed with compounds which contain the constituent elements of the heteropolyacid catalyst and/or a compound or compounds which contain an element or elements other than the constituent elements of the heteropolyacid catalyst.

4. The method according to claim 3, in which the nitrogen-containing heterocyclic compound is selected from the group consisting of pyridine, piperidine, piperazine, pyrimidine, isoquinoline and their derivatives.

5. The method according to claim 2, in which the nitrogen-containing heterocyclic compound is selected from the group consisting of pyridine, piperidine, piperazine, pyrimidine, isoquinoline and their derivatives.

6. The method according to claim 1, wherein the deteriorated catalyst and the nitrogen-containing heterocyclic compound are mixed with compounds which contain the constituent elements of the heteropolyacid catalyst and/or a compound or compounds which contain an element or elements other than the constituent elements of the heteropolyacid catalyst.

7. The method according to claim 6, in which the nitrogen-containing heterocyclic compound is selected from the group consisting of pyridine, piperidine, piperazine, pyrimidine, isoquinoline and their derivatives.

8. The method according to claim 1, in which the nitrogen-containing heterocyclic compound is selected from the group consisting of pyridine, piperidine, piperazine, pyrimidine, isoquinoline and their derivatives.

* * * * *